US00PP31150P2

(12) United States Plant Patent
Ranney

(10) Patent No.: US PP31,150 P2
(45) Date of Patent: Dec. 3, 2019

(54) ***RHODODENDRON* PLANT NAMED 'NCRX1'**

(50) Latin Name: *Rhododendron hybrida*
Varietal Denomination: NCRX1

(71) Applicant: North Carolina State University, Raleigh, NC (US)

(72) Inventor: Thomas Green Ranney, Arden, NC (US)

(73) Assignee: North Carolina State Universtiy, Raleigh, NC (US)

( * ) Notice: Subject to any disclaimer, the term of this patent is extended or adjusted under 35 U.S.C. 154(b) by 0 days.

(21) Appl. No.: 15/999,226

(22) Filed: Aug. 16, 2018

(51) Int. Cl.
*A01H 5/02* (2018.01)
*A01H 6/36* (2018.01)

(52) U.S. Cl.
USPC ..... Plt./239

(58) Field of Classification Search
USPC ..... Plt./239, 238
See application file for complete search history.

*Primary Examiner* — Susan McCormick Ewoldt
(74) *Attorney, Agent, or Firm* — Cassandra Bright

(57) ABSTRACT

A new and distinct *Rhododendron* cultivar named 'NCRX1' is disclosed, characterized by red-toned flower buds that mature into pink flower with wavy petal margins. Plants have a compact habit, are floriferous and consistent in flower production even at a young age, propagate readily from stem cuttings, and demonstrate good growth and survival when grown in full sun in unamended clay loam soils. The new cultivar is a *Rhododendron*, suitable for ornamental garden purposes.

3 Drawing Sheets

Latin name of the genus and species: *Rhododendron hybrida.*

Variety denomination: 'NCRX1'.

BACKGROUND OF THE INVENTION

The present invention comprises a new and distinct hybrid *Rhododendron* cultivar hereinafter referred to by the cultivar name 'NCRX1'. Developed by a breeding program in Mills River, N.C., 'NCRX1' was selected for its growth and survival in full sun and clay loam soils as well as its ornamental characteristics. 'NCRX1' was obtained from a population of seedlings derived from a controlled cross of the seed parent *Rhododendron* 'Pride's Early Red' (unknown parentage, unpatented) x the pollen parent *Rhododendron hyperythrum* 2006-029 (unpatented) in 2007. *Rhododendron* 'Pride's Early Red' was used as a parent because of its cold hardiness (USDA Zone 5) and dark red flower color. *Rhododendron hyperythrum*, a species native to Taiwan, was used as a parent because of its heat tolerance and resistance to *Phytophthora* root rot (Arisumi et al., 1986; Hoitink and Schmitthenner, 1975).

The first asexual propagation of 'NCRX1' occured in July 2010 by rooting stem cuttings at a research nursery in Mills River, N.C. 'NCRX1' roots readily from firm softwood cuttings treated with a basal dip of 5,000 ppm indole butyric acid (potassium salt) in water. 'NCRX1' has been found to retain its distinctive characteristics through successive asexual propagations over the course of 8 years. At least three generations have been reproduced and have shown that the unique features of this cultivar are stable and reproduced true to type.

SUMMARY OF THE INVENTION

The following are the unique combination of characteristics of this new cultivar when grown under standard horticultural practices at Mills River, N.C.

1. Showy flowers with dark red buds opening to various shades of pink with wavy petal margins.
2. Profuse and consistent flowering.
3. Compact habit.
4. Ease of propagation via stem cuttings.
5. Demonstrates good growth and survival when grown in full sun in unamended clay loam soils.

COMPARISON TO PARENT VARIETIES

'NCRX1' is similar in most horticultural characteristics to the seed parent. Plants of the new cultivar 'NCRX1' however differ in the following:

1. The new variety has pink flowers, the seed parent has dark red flowers.
2. Petal margins of the new variety are undulating, petal margins of the seed parent are non-undulating.

'NCRX1' is similar in most horticultural characteristics to the pollen parent. Plants of the new cultivar 'NCRX1' however differ in the following:

1. The new variety has pink flowers, the pollen parent has white flowers.
2. Petal margins of the new variety are undulating, petal margins of the pollen parent are non-undulating.

COMMERCIAL COMPARISON

'NCRX1' can be compared to the commercial variety *Rhododendron hybrida* 'PKT2011', unpatented. Plants of the new cultivar 'NCRX1' are similar to plants of 'PKT2011' in most horticultural characteristics. Plants of the new cultivar 'NCRX1', however, differ in the following:

1. Flowers of the new variety are lighter pink than flowers of this comparator.
2. Flower buds of the new variety have more red tones than flower buds of this comparator.

3. Petal margins of the new variety are undulating, flower margins of this comparator are non-undulating.

BRIEF DESCRIPTION OF THE PHOTOGRAPHS

'NCRX1' is illustrated by the accompanying photographs which show the plant's form, foliage, and inflorescences. The colors shown are as true as can be reasonably obtained by conventional photographic procedures. Colors in the photographs may differ slightly from the color values cited in the detailed botanical description, which accurately describe the colors of the new hybrid *Rhododendron*.

DETAILED BOTANICAL DESCRIPTION

Figure 1:
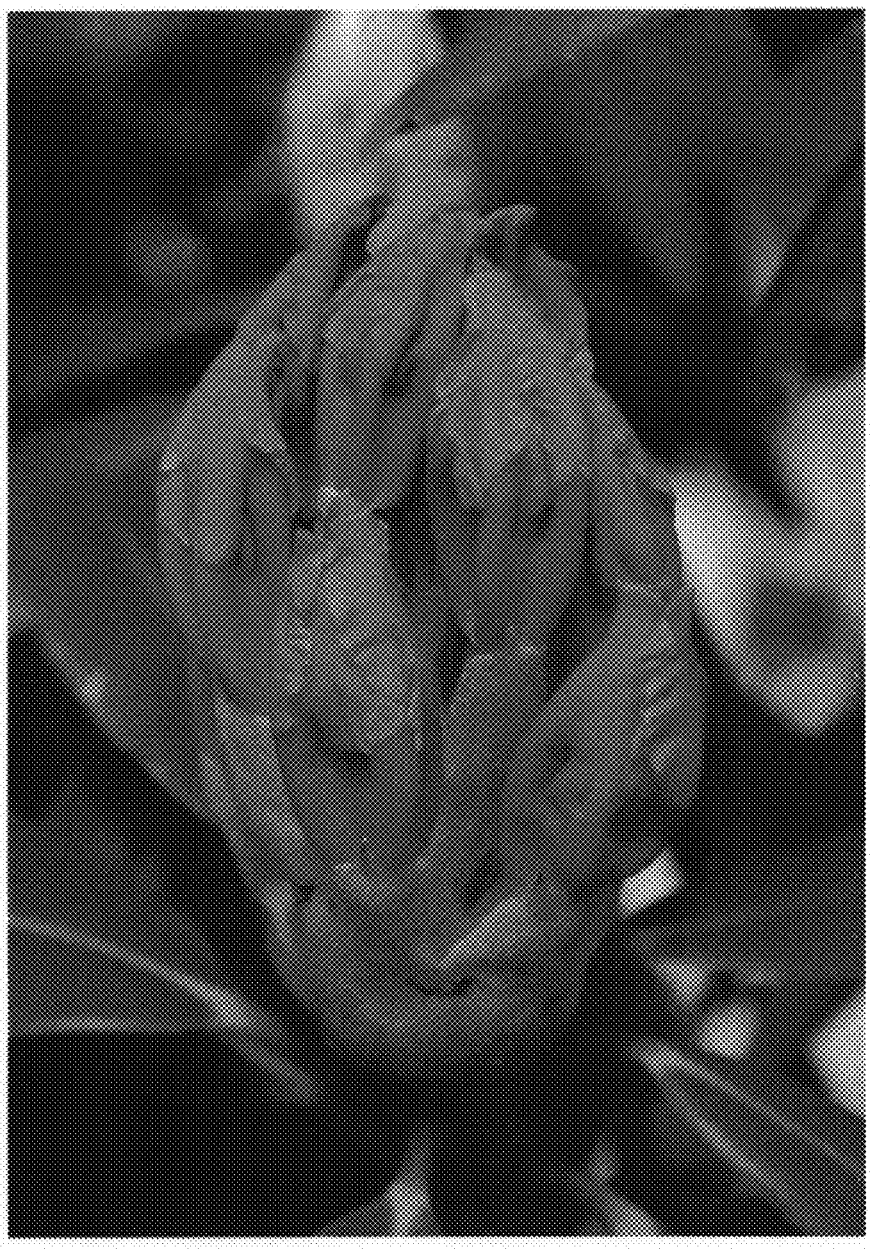
FIG. 1 shows the color of the expanding flower buds and inflorescences of 'NCRX1' on a 3-year-old, container-grown plant in a greenhouse in Mills River, N.C., in March 2016.
Figure 2:
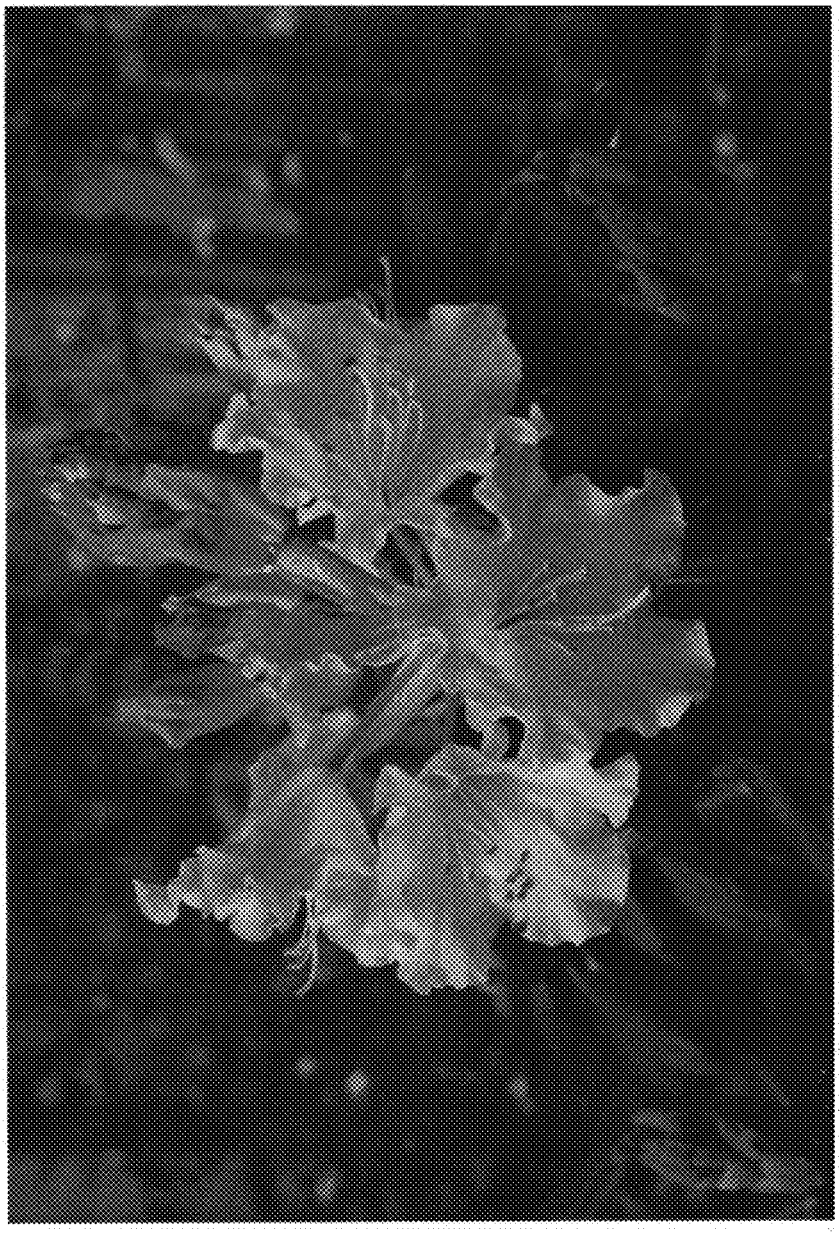
FIG. 2 shows the inflorescence with flower colors at different stages of development on a 3-year-old, container-grown plant in a greenhouse in Mills River, N.C., in March 2016.
Figure 3:
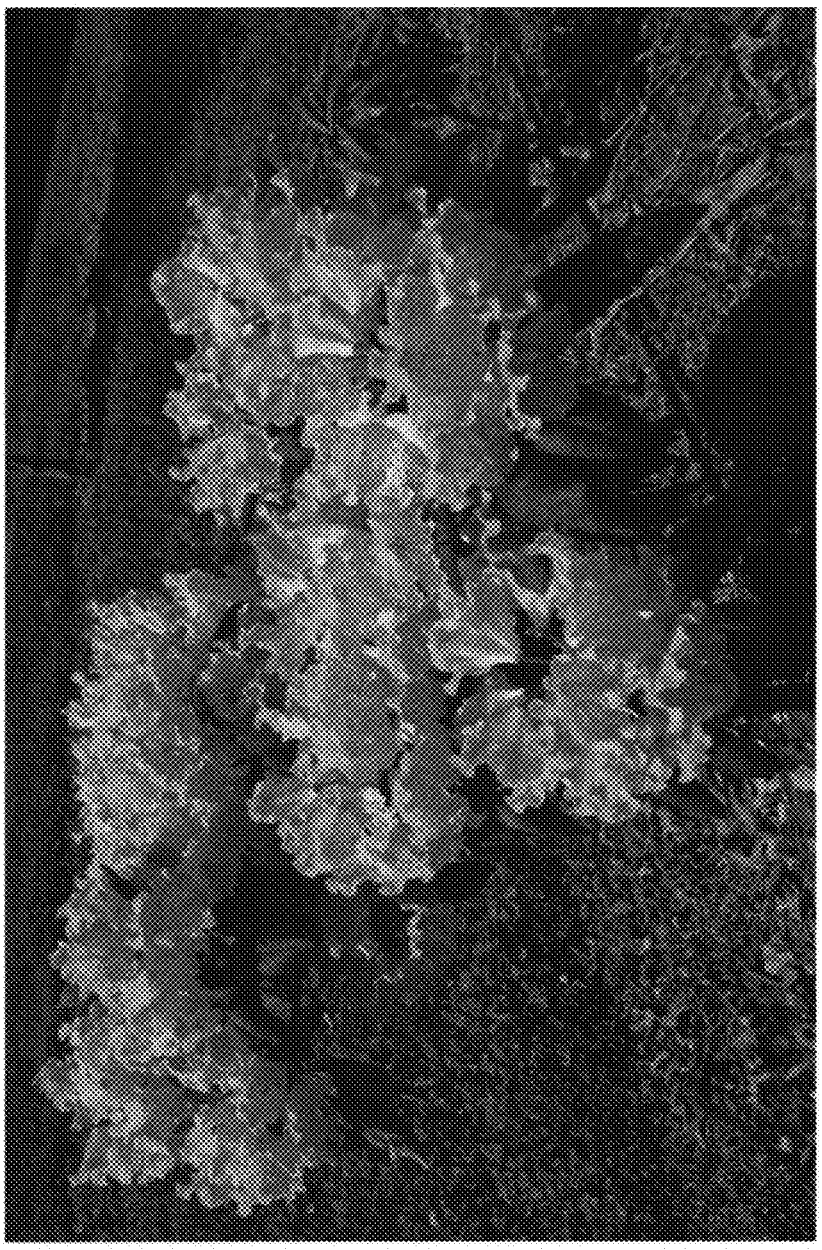
FIG. 3 shows the flowers and habit of a 4-year-old, field-grown plant in Mills River, N.C., in May 2012.

The following is a detailed description of the botanical characteristics of the new and distinct hybrid *Rhododendron* known by the denomination 'NCRX1'. The detailed description was taken on a 3-year-old container-grown plant in Mills River, N.C. in 2017. All colors cited herein refer to The Royal Horticultural Society Colour Chart (The Royal Horticultural Society (R.H.S.), London, 2015 Edition. Where specific dimensions, sizes, colors, and other characteristics are given, it is to be understood that such characteristics are approximations or averages set forth as accurately as practicable.

Botanical classification: *Rhododendron* 'NCRX1'.

PROPAGATION

Typically by firm softwood cuttings.

PLANT

Plant type: Evergreen shrub.
Growth habit: Rounded and upright, densely branched.
Height: 1 m after 7 years.
Width: 1.5 m after 7 years.
Growth rate: Moderate.
Roots: Fibrous.
Shoots (new growth):
- *Shape*.—Round.
- *Color*.—RHS 142A (Strong Yellow Green) with some blushing in RHS 34C (Strong Reddish Orange) and RHS 34D (Strong Yellowish Pink) on the adaxial side of the stems.
- *Texture*.—Slightly pubescent on new growth; glabrous with age.
- *Pubescence*.—RHS 27B (Light Yellowish Pink).

Branching characteristics: Well-branched, dense.
Shape: Rounded, but variable.
Color: Coloration varies depending upon the age of the branch. Branches that are 1 to 2 years old vary from and include RHS 144A/B (Strong Yellow Green), RHS 166A (Greyish Brown), RHS 166A (Greyish Brown), and RHS 166B (Moderate Reddish Brown). Branches older than 2 years exhibit a mix of RHS 200C (Light Brownish Grey) and RHS 199A, B, C and D, colors streaked together (Grey-Brown group). Where bark exfoliates, the epidermis is RHS 166D (Moderate Orange).
Texture: Glabrous to exfoliating.
Age of plant described: Approximately 7 years.

FOLIAGE

Leaf:
- *Type*.—Evergreen.
- *Arrangement*.—Alternate.
- *Attachment*.—Petiolate.
- *Division*.—Simple.
- *Shape*.—Predominantly elliptic or oblong.
- *Length*.—Average 9.44 cm.
- *Width*.—Average 3.42 cm.
- *Apex*.—Broadly acute.
- *Base*.—Rounded to broadly acute.
- *Margin*.—Entire; revolute on mature leaves.
- *Surface*.—Glaborous.
- *Color*.—Immature leaf, upper surface: Mix of RHS144A and RHS 147C. Pubescence: RHS 26B to RHS 26C. Immature leaf, lower surface: Mix of RHS147C and RHS 147D. Pubescence: RHS 157B. Mature leaf, upper surface: RHS 147A. Mature leaf, lower surface: RHS 146B.

Petiole:
- *Shape*.—Round.
- *Length*.—Average 2.18 cm.
- *Diameter*.—Average 3.32 mm.
- *Texture*.—Glaucous. Some petioles may retain limited pubescence into maturity.
- *Color*.—Upper and lower sides vary from and include RHS 147A (Moderate Olive Green) to RHS146B (Moderate Yellow Green). Pubescence, when present, ranges in color from RHS 165B (Brownish Orange) to RHS 165C (Moderate Orange Yellow) and in some instances RHS 165D (Pale Yellow).

FLOWER

Bloom period: Natural flowering begins in May, under conditions found in Michigan.
Flower:
- *Arrangement*.—Axillary clusters of perfect, single funnel shaped individual flowers. Typically 2 to 5 flowers per cluster. About 160 flowers and buds on a plant in full bloom. Flower longevity approximately 3 weeks.

Inflorescence:
- *Diameter*.—Average range 7-12 cm.

Flowers:
- *Length*.—Average 4.0 cm.
- *Diameter*.—Average 6.0 cm.
- *Facing direction*.—Outwardly and upwardly facing.
- *Persistent or self-cleaning*.—Self-cleaning.
- *Fragrance*.—None.

Petals:
- *Length*.—Approximately 2.5 cm.
- *Width*.—Approximately 1.5 to 2.0 cm.
- *Apex*.—Acute, undulating and ruffled.
- *Base*.—Fused.
- *Shape of petal*.—Ovate.
- *Petal margin*.—Entire, undulating, wavy to ruffled.
- *Petal Number*.—5.
- *Petal texture, upper and lower surfaces*.—Smooth.

*Color*.—While Opening: Adaxial (upper) surface: Petals are a mix of RHS 73C (Light Purplish Pink) and RHS 73D (Very Pale Purple). Blotch: Mix of RHS 73D (Very Pale Purple) and RHS 155A (Pale Yellow Green). Abaxial (lower) surface: Predominantly RHS 61C (Vivid Purplish Red) fading to RHS 63D (Light Purplish Pink) at tips: RHS 69C (Very Pale Purple) at the base. Open/Anthesis: Adaxial (upper) surface: Petal tips are a mix of RHS 75C (Very Light Purple) and RHS 75D (Very Pale Purple), which deepens to RHS 65B (Light Purplish Pink) along the petal midrib. Blotch: Visible on the uppermost petal on the adaxial side, coloration is slight: RHS 155A (Pale Yellow Green). Abaxial (lower) surface: Deeper pigmentation is visible along the midrib of the petal in RHS 63A/B (Strong Purplish Red), which fades to a mix of RHS N66D (Deep Purplish Pink) and RHS 76D (Very Pale Purple). Fuse points and petal bases are RHS 76D (Very Pale Purple).

Bud:

*Shape*.—Obovate to elliptic.
*Length*.—Average 2.6 cm.
*Diameter*.—Average 1 cm.
*Color*.—RHS 76D at base, to variable colors ranging from RHS 58B/C to RHS N57D. Tips are RHS 58B, with blushing in RHS 60D.

Flower tube:

*Length*.—Average 7-10 mm.
*Color, outer surface*.—RHS Red-Purple 73D.
*Color, inner surface*.—RHS Green 143D.

Calyx/sepals: Star shaped calyx.

*Quantity per flower*.—5 sepals.
*Shape*.—Lanceolate.
*Length*.—9 mm.
*Width*.—3 mm.
*Apex*.—Narrowly acute.
*Base*.—Fused.
*Margin*.—Entire.
*Texture*.—All surfaces slightly pubescent.
*Color*.—Interior Surface: Near RHS Yellow-Green 145D. Outer Surface: Near RHS Yellow-Green 145D.

Peduncle: Not present, inflorescence pedicels emerge directly from node.

Pedicel:

*Length*.—Average 5 mm.
*Diameter*.—1 mm.
*Color*.—Near RHS Yellow-Green 145D, tinged near Red-Purple 57A.
*Texture*.—Slightly pubescent.
*Aspect*.—Straight. Angle of attachment, approximately 45° angle from stem.
*Strength*.—Strong.

REPRODUCTIVE ORGANS

Stamens:

*Number*.—5.
*Filament length*.—3 cm.
*Width*.—0.1 cm.
*Filament color*.—Near RHS Red-Purple 57A.
*Shape*.—Spherical.
*Length*.—Less than 1 mm.
*Color*.—Near RHS Red-Purple 72A.
*Pollen*.—Scant, colored near Red-Purple 57A.

Pistil:

*Number*.—1.
*Length*.—Average 3.2 cm.
*Style*.—Length: Average 3.0 cm. Color: Near RHS Red-Purple N57C.
*Stigma*.—Globular, colored near Red-Purple N66A.
*Ovary*.—Colored near White 155C.

OTHER CHARACTERISTICS

Disease and pest resistance: Not observed to be susceptible nor resistant to normal diseases and pests of *Rhododendron*.

Temperature tolerance: Observed hardy to USDA Zone 7, potentially hardy to zone 6.

Fruit/seed production: Not observed to date.

What is claimed is:

1. A new and distinct cultivar of *Rhododendron* plant named 'NCRX1' as herein illustrated and described.

* * * * *